(12) United States Patent
Haubrich et al.

(10) Patent No.: US 8,791,439 B2
(45) Date of Patent: Jul. 29, 2014

(54) PARTICULATE COMPOSITIONS HAVING PLURAL RESPONSES TO EXCITATION RADIATION

(75) Inventors: Scott Haubrich, Albuquerque, NM (US); Jainisha Shah, Rio Rancho, NM (US); Steven R. Cordero, Albuquerque, NM (US)

(73) Assignee: Cabot Security Materials, Inc., Albuquerque, NM (US)

( * ) Notice: Subject to any disclaimer, the term of this patent is extended or adjusted under 35 U.S.C. 154(b) by 159 days.

(21) Appl. No.: 13/496,663

(22) PCT Filed: Oct. 1, 2010

(86) PCT No.: PCT/US2010/051092
§ 371 (c)(1),
(2), (4) Date: Mar. 16, 2012

(87) PCT Pub. No.: WO2011/041657
PCT Pub. Date: Apr. 7, 2011

(65) Prior Publication Data
US 2012/0175528 A1 Jul. 12, 2012

Related U.S. Application Data

(60) Provisional application No. 61/247,693, filed on Oct. 1, 2009.

(51) Int. Cl.
*G01J 1/00* (2006.01)
*H04N 5/33* (2006.01)
*G01J 3/10* (2006.01)
*F41J 2/02* (2006.01)

(52) U.S. Cl.
CPC . *H04N 5/33* (2013.01); *G01J 3/108* (2013.01); *F41J 2/02* (2013.01)
USPC ..................................................... 250/495.1

(58) Field of Classification Search
USPC ............................................ 250/458.1, 459.1
See application file for complete search history.

(56) References Cited

U.S. PATENT DOCUMENTS 4,249,108 A 2/1981 Wolfe
6,180,029 B1 1/2001 Hampden-Smith et al.
(Continued)

FOREIGN PATENT DOCUMENTS

DE 10 2005 032831 1/2007
KR 2006 087 637 A1 8/2006

OTHER PUBLICATIONS

Sang Hyuk Han et al., "Characterization of Luminescent Properties of Sr-Ca-Al-O Multi-phase Oxide Phosphors", Journal of Electrocermaics, Kluwer Academic Publishers, BO,. vol. 21, No. 1-4, Aug. 17, 2007, pp. 715-718, XP019678770, ISSN: 1573-8663.

*Primary Examiner* — David Porta
*Assistant Examiner* — Adam J Fifth (57) ABSTRACT

A particulate composition comprises a plurality of particles wherein at least one of the particles comprises at least two different crystalline and/or glass phases, each phase comprising a host lattice and a dopant sensitive to electromagnetic radiation. The different phases simultaneously produce different responses on exposure to photons of the same energy, whereby the output from the particulate composition when exposed to said photons is the sum of the responses from the different phases.

13 Claims, 8 Drawing Sheets

(56) References Cited

U.S. PATENT DOCUMENTS

| | | | |
|---|---|---|---|
| 6,528,165 B2 * | 3/2003 | Chandler | 428/402.2 |
| 2006/0162497 A1 | 7/2006 | Kodas et al. | |
| 2006/0165898 A1 | 7/2006 | Kodas et al. | |
| 2006/0165910 A1 | 7/2006 | Kodas et al. | |
| 2006/0166057 A1 | 7/2006 | Kodas et al. | |
| 2007/0096057 A1 | 5/2007 | Hampden-Smith | |
| 2008/0160343 A1 | 7/2008 | Nazarov et al. | |
| 2009/0007815 A1 * | 1/2009 | Hampden-Smith et al. | 106/31.13 |

* cited by examiner

PARTICULATE COMPOSITIONS HAVING PLURAL RESPONSES TO EXCITATION RADIATION

CROSS-REFERENCE TO RELATED APPLICATIONS

This application is a §371 national phase application of and claims priority to PCT/US2010/051092, filed on Oct. 1, 2010, which claims priority to U.S. Provisional Patent Application No. 61/247,693, filed on Oct. 1, 2009, both hereby incorporated by reference in their entirety.

FIELD

This invention relates to particulate compositions having plural responses to excitation radiation and their use in security applications.

BACKGROUND

Phosphors are compositions that are capable of emitting useful quantities of radiation in the visible, infrared and/or ultraviolet spectrums upon excitation of the phosphor compound by an external energy source. Due to this property, phosphor compounds have long been utilized in cathode ray tube (CRT) screens for televisions and similar devices, as taggants for authenticating documents and products, and as luminescent coatings in fluorescent lamps, x-ray scintillators, light emitting diodes, and fluorescent paints. Typically, inorganic phosphor compounds include a host lattice containing a small amount of an emitter or dopant ion.

Conventional phosphor compositions have a defined response (e.g., emission) to a given excitation by electromagnetic radiation. Phosphor compositions may, for example, convert one wavelength to a second wavelength whether ultraviolet to visible, ultraviolet to infrared, visible to visible, visible to infrared, infrared to infrared, or infrared to visible. Phosphor compositions may also emit near the wavelength they absorb.

When used in security applications, phosphor compositions are applied to articles to be authenticated and some basic property of the phosphor, generally the wavelength of the emitted radiation, is monitored by a detector to provide an indication or "tag" of whether an article being tested in genuine. In some applications, it is necessary to differentiate between a series of tagged articles and, although this can be achieved by applying different phosphor compositions which emit radiation of different wavelengths, this has the disadvantage of requiring a monitoring system with multiple detectors capable of separating and reading the different wavelengths.

For certain applications, including differentiation between a series of tagged articles, it would be advantageous to have phosphor compositions that can controllably emit different responses, e.g., emissions, to a single or multiple energy sources. For example, U.S. Published Patent Application No. 2009/0007815 discloses a particulate composition having a first response to a first electromagnetic radiation and, after intermediate exposure to a second electromagnetic radiation, a second response to the first electromagnetic radiation, different from the first response.

According to the present invention, a multiphase photosensitive particle is provided, in which the same particle contains multiple different phases, each producing a different response when excited by radiation of the same energy or different energies so that the overall output of the particle is equal to the sum of the responses between the phases. By varying the relative amounts of the different phases it is possible to produce a series of particles with different outputs useful in security applications requiring authentication and differentiation between articles.

SUMMARY

In one aspect, the invention resides in a particulate composition comprising at least one particle having at least two different crystalline and/or glass phases, each phase comprising a host lattice and a dopant sensitive to electromagnetic radiation and the different phases simultaneously producing different responses on exposure to photons of the same energy or different energies, whereby the output from the particulate composition when exposed to said photons is the sum of the responses from the different phases.

Conveniently, each phase is sensitive to electromagnetic radiation in the UV, visible or IR regions of the electromagnetic spectrum.

Conveniently, the different phases produce different emission spectra on exposure to photons of the same energy.

In one embodiment, the different phases produce emission spectra with peaks at different wavelengths on exposure to photons of the same energy.

In another embodiment, each phase produces an emission spectrum with multiple peaks on exposure to photons of the same energy and the ratio of the relative intensities of the peaks differs between the phases.

In yet another embodiment, the different phases emit radiation having different decay rates on exposure to photons of the same energy.

In a further embodiment, the phases have different selective absorbance to photons of the same energy.

Alternatively, the phases have different extinction coefficients for photons of different energy.

In a further aspect, the invention resides in a method for authenticating and differentiating between a series of articles, the method comprising:

(a) applying to each article a particulate composition comprising a plurality of particles wherein at least one of the particles comprises at least two different crystalline and/or glass phases, each phase comprising a host lattice and a dopant sensitive to electromagnetic radiation and the different phases simultaneously producing different responses on exposure to photons of the same energy or different energies, whereby the output from the particulate composition when exposed to said photons is the sum of the responses from said different phases;

(b) varying the ratio of the amounts of the different phases in the particulate compositions applied to the different articles whereby each article produces a different output on exposure to said photons of the same or different energies;

(c) exposing each article to photons of the same or different energies; and (d) measuring the output from each article.

BRIEF DESCRIPTION OF THE DRAWINGS

FIGS. 1(a) and (b) are X-ray diffraction (XRD) patterns of the composite materials C-1 and C-2 respectively of Example 1.

FIGS. 3(a) to (c) compare the PL emission spectra of the individual pure $(Y_{0.92}Eu_{0.08})_2O_3$ and $(Y_{0.92}Eu_{0.08})_3PO_7$ components (FIG. 3a), the mixture M1 and composite C-1 (FIG.

3b), and the mixture M-2 and composite C-2 (FIG. 3c) after excitation with 365 nm UV light.

FIGS. 3(d) to (f) compare the PL emission spectra of the individual pure $(Y_{0.92}Eu_{0.08})_2O_3$ and $(Y_{0.92}Eu_{0.08})_3PO_7$ components (FIG. 3d), the mixture M1 and composite C-1 (FIG. 3e), and the mixture M-2 and composite C-2 (FIG. 3f) after excitation with 254 nm UV light.

FIGS. 8 (a) to (c) are SEM images of pure $(Y_{0.92}Eu_{0.08})_2O_3$, pure $(Y_{0.92}Eu_{0.08})_4Al_2O_9$ and composite C-6 respectively.

FIGS. 9(a) and (b) compare the PL emission spectra of the individual pure $(Y_{0.92}Eu_{0.08})_2O_3$ and $(Y_{0.92}Eu_{0.08})_4Al_2O_9$ components (FIG. 9a) and the composite C-6 and the mixture M-6 (FIG. 9b) after excitation with 365 nm UV light.

FIGS. 9(c) and (d) compare the PL emission spectra of the individual pure $(Y_{0.92}Eu_{0.08})_2O_3$ and $(Y_{0.92}Eu_{0.08})_4Al_2O_9$ components (FIG. 9c) and the composite C-6 and the mixture M-6 (FIG. 9d) after excitation with 254 nm UV light.

FIGS. 10(a) and (b) are XRD patterns of the composites C-7 and C-8 respectively of Example 4.

DETAILED DESCRIPTION OF THE EMBODIMENTS

Described herein is a particulate composition comprising a plurality of particles wherein at least one, and preferably substantially all, of the particles comprises at least two different crystalline and/or glass phases and wherein each phase comprises a host lattice and a dopant sensitive to electromagnetic radiation. Moreover, the different phases are selected so that they simultaneously produce different responses on exposure to photons of the same energy or different energies. In this way the output from the particulate composition when exposed to such photons is the sum of the responses from the different phases.

Since the output of the composition in response to excitation is equal to the sum of the responses from the different phases, by varying the relative amounts of the phases, it is possible to produce a series of particulate compositions each with a different characteristic output. This facility is particularly useful in security applications when it is necessary not only to authenticate a single article, but also to differentiate between different authentic articles, for example, banknotes of different denominations. Thus, by applying a different particulate composition, each with a unique ratio between the amounts of the different phases, to each article to be authenticated, it is possible to measure the output from the different compositions in response to excitation radiation to uniquely identify each article.

Depending on the selection of the particular host lattice/dopant combination, particulate compositions as described herein can be produced so as to be sensitive to electromagnetic radiation over a wide range of the electromagnetic spectrum. For many practical applications, preference may be given to compositions sensitive to radiation in the UV, visible or IR regions of the spectrum, but in other applications it may be useful to produce compositions sensitive to radiation in one or more of the radio, microwave, X-ray and gamma ray regions of the spectrum.

In one embodiment, the present particulate composition comprises at least one particle having at least two different crystalline and/or glass phases which behave as photoluminescent phosphors with different emission characteristics in response to exposure to photons of a given energy. For example, the different phases can be arranged to produce emission spectra with peaks at different wavelengths on exposure to said photons of the same energy. Alternatively, each phase can be arranged to produce an emission spectrum with multiple peaks on exposure to photons of the same energy but with the ratio of the relative intensities of the peaks differing between the phases. As a further alternative, the different phases can be arranged to emit radiation having different decay rates on exposure to said photons of the same energy.

In principal, where the different phases in the particulate composition behave as photoluminescent phosphors, any known phosphor host lattice may be used in each phase if it is possible to incorporate at least one type of luminescent dopant atom into said host lattice to result in a luminescent composition. Examples of host lattices which may be useful include compounds comprising a cation containing at least one element selected from Groups 2, 3 12, and 13 of the Periodic Table and the lanthanide elements, and an anion containing at least one element selected from Groups 13, 14, 15, 16 and 17 of the Periodic Table. Typically, the or each cation element is selected from yttrium, lanthanum, gadolinium, lutetium, zinc, magnesium, calcium, strontium, and barium and the or each anion element is selected from boron, aluminum, gallium, silicon, germanium, nitrogen, phosphorous, arsenic, oxygen, sulfur, selenium, fluorine, chlorine, bromine, iodine. Particular lattice materials suitable for use in the present phosphor compositions include yttrium oxide, yttrium phosphate, yttrium sulfides, yttrium oxysulfides, yttrium aluminates, such as $Y_3Al_5O_{12}$ (YAG), $YAlO_3$ (YAP) and $Y_4Al_2O_9$ (YAM), and yttrium silicon nitrides and oxynitrides, such as $YSi_3N_5$ and $Y_2Si_{11}N_{20}O$, erbium aluminates, such as $Er_3Al_5O_{12}$ and $ErAlO_3$ (YAP), barium magnesium aluminates, gadolinium oxide and gadolinium gallates, such as $Gd_3Ga_5O_{12}$, lanthanum oxide, lanthanum phosphate, neodymium phosphate, zirconia, ceria, zinc silicates, and strontium silicates. Mixed lattice compositions can also be employed.

The dopants employed herein are typically ions of lanthanide elements, including cerium, praseodymium, neodymium, samarium, europium, terbium, dysprosium, holmium, erbium, thulium, ytterbium and mixtures thereof. Other elements that can be used as the dopant ion in the present particulate composition include magnesium, chromium, manganese, cobalt, ion), renium, osmium, molybdenum, titanium, copper, silver, nickel, tin, lead, zinc and mixtures thereof. Generally, the dopant is present as an oxygen-containing compound, such as a metal oxide, a silicate, borate, phosphate, oxysulfide or aluminate.

The amount of dopant present in the luminescent composition is not narrowly defined and generally can range from about 0.1 to about 99 mole %, such as from about 1 to about 80 mole %, for example from about 5 to about 70 mole %, conveniently from about 5 to about 25 mole % of the total luminescent composition.

In producing particulate phosphor compositions with different emissions from the same particle, use is made of the fact that the host structure and site symmetry of a phosphor material strongly influence its spectral properties. Thus, for example, europium doped yttrium oxide and europium doped yttrium phosphate have different site symmetries, host structures and host lattices and so, when excited, generally have different emission spectra and decay rates. The lifetime for the decay of the oxide emission is 1.15 ms, whereas that for the phosphate emission is 3.0 ms. It is therefore possible to tune the observable decay rate to any value in the range 1.15 to 3.0 ms, by making particles with varying amounts of the mixed phases.

In addition, as shown in Table 1, different rare earth phosphates have different crystal structures, for example the xenotime phase and the monazite phase, with different rare earth (RE) to rare earth distances. The longer these distances, there is less orbital overlap and cross talk between the dopants, which in turn leads to less concentration quenching of the dopants and hence longer decay times.

TABLE 1

| Phosphate | Space group | Symmetry | RE-RE distance (Å) |
| --- | --- | --- | --- |
| $YPO_4$ | 141/amd | Tetragonal | 3.7-5.2 |
| $EuPO_4$ | P121/n1(14) | Monoclinic | 4.0-5.9 |
| $LaPO_4$ | P121/n1(14) | Monoclinic | 4.1-5.9 |
| $YbPO_4$ | 141/amd | Tetragonal | 3.7-5.9 |
| $Nd_3PO_7$ | C1M1(8) | Monoclinic | 3.7-5.9 |

In another embodiment, the present particulate composition comprises at least one particle having at least two different crystalline and/or glass phases which have different selective absorbance to photons of the same energy due to the phases having different extinction coefficients at the wavelength of the photons. As a result the amount of incident radiation absorbed by the particulate composition will depend on the relative amounts of the different phases in the composition.

Alternatively, the present particulate composition comprises at least one particle having at least two different crystalline and/or glass phases which have different extinction coefficients to photons of different wavelength. Thus, when exposed to a mixed radiation source, the distribution of wavelengths in the output from the particulate composition will depend on the relative amounts of the different phases in the composition.

Typically, the present particulate composition is in the form of particles having a small average size. Although the preferred average size will vary according to the application of the composition, in most cases the average particle size is less than about 10 μm, preferably less than about 5 μm, more preferably less than about 3 μm, such as from about 0.1 μm to about 3 μm, typically about 2 μm. As used herein, the average particle size is the weight average particle size.

Generally, it is preferred that the particulate composition also has a narrow particle size distribution, such that the majority of particles are substantially the same size. Preferably, at least about 90 weight percent of the particles and more preferably at least about 95 weight percent of the particles are not larger than twice the average particle size. Thus, when the average particle size is about 2 μm, it is preferred that at least about 90 weight percent of the particles are not larger than 4 μm and it is more preferred that at least about 95 weight percent of the particles are not larger than 4 μm. Further, it is preferred that at least about 90 weight percent of the particles, and more preferably at least about 95 weight percent of the particles, are not larger than about 1.5 times the average particle size. Thus, when the average particle size is about 2 μm, it is preferred that at least about 90 weight percent of the particles are not larger than about 3 μm and it is more preferred that at least about 95 weight percent of the particles are not larger than about 3 μm.

The particles are also preferably substantially spherical in shape. That is, the particles are not jagged or irregular in shape. Spherical particles are particularly advantageous because they are able to disperse and coat an article more uniformly with a reduced average thickness. Although the particles are substantially spherical, the particles may become faceted as the crystallite size increases and approaches the average particle size.

The individual components of the particles advantageously have a high degree of purity, that is, a low level of impurities. Impurities are those materials that are not intended in the final product. Thus, the dopant ion is not considered as an impurity. The level of impurities in the present phosphor powders is preferably not greater than about 1 atomic percent, more preferably not greater than about 0.1 atomic percent, and even more preferably not greater than about 0.01 atomic percent.

In one embodiment, the phosphor particles are provided with a surface coating that substantially encapsulates the outer surface of the particles. Such coatings can assist in reducing degradation of the phosphor material due to moisture or other influences and can also create a diffusion barrier such that activator ions cannot transfer from one particle to another, thereby altering the luminescence characteristics. Coatings can also control the surface energy levels of the particles. It is to be appreciated that any coating on the particles of the present composition is not considered as one of the two different crystalline and/or glass phases present in one or each particle of the composition.

The coating can be a metal, metal oxide or other inorganic compound such as a metal sulfide, or can be an organic compound. For example, a metal oxide coating can advantageously be used, such as a metal oxide selected from the group consisting of $SiO_2$, $MgO$, $Al_2O_3$, $ZnO$, $SnO_2$ or $In_2O_3$. Particularly preferred are coatings are $SiO_2$ and $Al_2O_3$. Semiconductive oxide coatings such as $SnO_2$ or $In_2O_3$ can also be advantageous in some applications due to the ability of the coating to absorb secondary electrons that are emitted by the phosphor. Metal coatings, such as copper, can be useful for phosphor particles used in direct current electroluminescent applications In addition, phosphate coatings, such as zirconium phosphate or aluminum phosphate, can also be advantageous for use in some applications.

The coating should encapsulate the entire particle, but should be sufficiently thin that the coating does not interfere with light transmission. Preferably, the coating has an average thickness of at least about 2 nanometers, more preferably at least about 5 nanometers, but not greater than about 200 nanometers, more preferably not greater than about 100 nanometers, and even more preferably not greater than about 50 nanometers. In one embodiment, the coating has a thickness of from about 2 to about 50 nanometers, such as from about 2 to about 10 nanometers. Further, the particles can include more than one coating substantially encapsulating the particles to achieve the desired properties.

The coating, either particulate or non-particulate, can also include a pigment or other material that alters the light characteristics of the phosphor. Red pigments can include compounds such as the iron oxides ($Fe_2O_3$), cadmium sulfide compounds (CdS) or mercury sulfide compounds (HgS). Green or blue pigments include cobalt oxide (CoO), cobalt aluminate ($CoAl_2O_4$) or zinc oxide (ZnO). Pigment coatings are capable of absorbing selected wavelengths of light leaving the phosphor, thereby acting as a filter to improve the color contrast and purity.

In addition, the phosphor particles can be coated with an organic compound, such as PMMA (polymethylmethacrylate), polystyrene or similar organic compounds, including surfactants that aid in the dispersion and/or suspension of the particles in a flowable medium. The organic coating is preferably not greater than about 100 nanometers thick and is substantially dense and continuous about particle. The organic coatings can advantageously prevent corrosion of the phosphor particles, especially in electroluminescent lamps, and also can improve the dispersion characteristics of the particles in a paste or other flowable medium.

The coating can also be comprised of one or more monolayer coatings, such as from about 1 to 3 monolayer coatings. A monolayer coating is formed by the reaction of an organic or an inorganic molecule with the surface of the phosphor particles to form a coating layer that is essentially one molecular layer thick. In particular, the formation of a monolayer coating by reaction of the surface of the phosphor powder with a functionalized organosilane such as halo- or amino-silanes, for example hexamethyldisilazane or trimethylsilylchloride, can be used to modify and control the hydrophobicity and hydrophilicity of the phosphor powders. Metal oxides (e.g. ZnO or $SiO_2$) or metal sulfides (e.g. $Cu_2S$) can also be formed as monolayer coatings. Monolayer coatings can allow for greater control over the dispersion characteristics of the phosphor powder in a wide variety of paste compositions and other flowable mediums.

The monolayer coatings may also be applied to phosphor powders that have already been coated with an organic or inorganic coating, thus providing better control over the corrosion characteristics (through the use of a thicker coating) as well as dispersibility (through the use of a monolayer coating) of the phosphor powder.

Although the present particulate composition can be produced by any known method which allows the production of a single particle with at least two different crystalline and/or glass phases, preferred methods include spray pyrolysis and pyrolysis using a flame reactor, as discussed in more detail below. Thus these methods not only facilitate preparation of multiphase particles but also generate spherical particles of the desired size and size distribution.

In spray pyrolysis, a precursor medium is produced which comprises a precursor to at least one the components of the phosphor composition dissolved or suspended in a liquid carrier, while the remaining components, if any, of the composition are dispersed as particles in the liquid carrier. The liquid carrier is then atomized to produce an aerosol comprising droplets dispersed and suspended in a carrier gas. The aerosol is then heated at a temperature of at least 200° C., generally from about 300° C. to about 1500° C., in order to: (1) remove at least a portion of the liquid carrier in the droplets; and (2) convert the or each precursor to the corresponding component of the particulate composition.

By the term "precursor" is meant any compound capable of being chemically converted under the conditions employed in the spray pyrolysis process to at least one component of the final particulate composition. Suitable precursors therefore include inorganic salts of the elements contained in the particulate composition, such as nitrates, sulfates and chlorides.

Generally, where the precursor medium contains solid particles of at least one component of the final particulate composition, the solid particles are arranged to have a particle size of between about 0.1 micron and about 100 micron, such as between about 1 micron and about 10 micron.

The precursor medium can be converted into aerosol form using any suitable device that disperses liquid into droplets, such as for example, a spray nozzle. Examples of suitable spray nozzles include ultrasonic spray nozzles, multifluid spray nozzles and pressurized spray nozzles. Ultrasonic spray nozzles generate droplets of liquid by using piezoelectric materials that vibrate at ultrasonic frequencies to break up a liquid into small droplets. Pressurized nozzles use pressure and a separator or screen in order to break up the liquid into droplets. In some cases, pressurized nozzles may involve use of some vapor that is generated from the liquid itself in order to pressurize and break up the liquid into droplets. One advantage of using ultrasonic and pressurized nozzles is that an additional fluid is not required to generate liquid droplets. This may be useful in situations where the precursor dissolved in the liquid vehicle is sensitive and/or incompatible with other common fluids used in multi-fluid spray nozzles.

In addition to the use of a spray nozzle for dispersing the liquid medium, any other suitable device or apparatus for generating disperse droplets of liquid may be used. One example of a device that is useful in generating droplets of liquid is an ultrasonic generator. An ultrasonic generator uses transducers to vibrate liquids at very high frequencies which break up the liquid into droplets. One example of an ultrasonic generator that is useful in the present process is disclosed in U.S. Pat. No. 6,338,809, incorporated herein by reference in its entirety. Another example of a device that is useful in generating droplets of liquid is a high energy atomizer such as those used in carbon black production.

Generally, whatever method is employed to atomize the precursor medium, the aerosol produced is arranged to have an average droplet size between about 1 and about 100 microns, such as between about 3 and about 50 microns, for example between about 5 and about 30 micron. In certain cases, it may be desirable to introduce one or more precursors and/or components of the final particulate composition to the spray conversion reactor as dry powders.

Further details of the spray pyrolysis process can be found in U.S. Pat. No. 6,180,029, and in U.S. Patent Application Publication No. 20070096057, the entire contents of which are hereby incorporated herein as if set forth herein in full. See also U.S. Patent Application Publication Nos. 20060166057, 20060165898, 20060165910; and 20060162497, the entireties of which are incorporated herein by reference.

In the flame reactor process, a nongaseous precursor of at least one component of the desired particulate composition is introduced into a flame reactor heated by at least one flame. The nongaseous precursor is introduced into the flame reactor in a very hot zone, also referred to herein as a primary zone, that is sufficiently hot to cause the component of the nongaseous precursor to be transferred into the gas phase of a flowing stream in the flame reactor, followed by a particle nucleation from the gas phase. In some embodiments, the temperature in at least some portion of this primary zone, and sometimes only in the hottest part of the flame, is high enough so that substantially all of materials flowing through that portion of the primary zone are in the gas phase. The component of the nongaseous precursor may enter the gas phase by any mechanism. For example, the nongaseous precursor may simply vaporize, or the nongaseous precursor may decompose and the component enter the gas phase as part of a decomposition product. Eventually, however, the component then leaves the gas phase as particle nucleation and growth occurs. Removal of the component from the gas phase may involve simple condensation as the temperature cools or may include additional reactions involving the component that results in a non-vapor reaction product. In addition to this primary zone where the component of the nongaseous precursor is transferred into the gas phase, the flame reactor may also include one or more subsequent zones for growth or modification of the nanoparticulates. In most instances, the primary zone will be the hottest portion within the flame reactor.

One suitable flame reactor is disclosed in U.S. Patent Application Publication No. 2006/0162497, published on Jul. 27, 2006, the entire contents of which are incorporated herein by reference. Using a flame reactor, conversion temperatures in excess of 1000° C., such as from about 1200° C. to about 3000° C. can be attained.

Multiphase particles of the type employed in the present particulate composition can be produced by the spray processes described above either in a single stage process or in multiple stages. For example, where a single stage process is employed, the feed to the pyrolysis step may contain precursors to two or more host lattice materials and to one or more dopant materials thereby allowing the formation of particles each containing different phosphorescent phases. Alternatively, a multistage process can be used in which a particle having a single phosphorescent phase is produced in a first pyrolysis stage and this particle is then used as part of the feed to a second pyrolysis stage.

The particulate compositions described herein can be employed to produce security features on articles such as credit cards, driver's licenses, passports, checks, currency, bonds, tickets, tax stamps, banknotes, cigarette pack tear tapes, thin films (e.g., for shrink wrap applications), security thread, ID cards and the like. As used herein, the term "security feature" means a feature that is placed on an article (e.g., a label, a document such as a passport, check, bond, banknote, currency, or ticket), directly or indirectly, for the purpose of authenticating the article. The particulate compositions can also be incorporated directly into packaging to authenticate packaged products.

This is conveniently achieved by combining the particulate composition with a liquid to form a flowable medium, such as an ink, paste or slurry, and then applying a coating comprising the composition onto a substrate. In addition to the particulate composition, such a flowable medium may comprise one or more of the following: a liquid vehicle, an anti-agglomeration agent, one or more additives (e.g., surfactants, polymers, biocides, thickeners, etc.), other particulates (metallic and/or non-metallic), and other components. The medium may be deposited onto a substrate by virtually any printing process, such as ink-jet printing, screen printing, intaglio printing, roll printing, lithographic printing and gravure printing.

The invention will now be more particularly described with reference to the following non-limiting Examples and the accompanying drawings.

All the individual and composite materials described in the Examples were made by spray pyrolysis using soluble metal precursors and phosphoric acid. The first step in spray pyrolysis was the formation of an aqueous solution comprising all the required elements in the form of soluble inorganic salts (metal nitrates) and (when needed) phosphoric acid in the desired ratios. Next, the liquid carrier was atomized with an ultrasonic generator using membrane transducers to produce an aerosol comprising droplets dispersed and suspended in compressed air as a carrier gas. The aerosol was then heated to a temperature high enough to ensure i) the removal of at least a portion of the liquid carrier in the droplets, ii) convert (decompose) the precursors to the corresponding components of the particulate composition. When necessary a final post treatment step at higher temperatures was added in order to complete the precursor conversion.

Powder X-ray diffraction (XRD) analyses were carried out on a Bruker D-8 Advance instrument using Ni-filtered Cu—K$\alpha$ radiation at 40 kV/40 mA. XRD patterns were recorded between 10 and 95 degrees 2$\theta$ at 0.02 deg/step and 1.25 sec/step collecting time. Initial phase identification was performed using the EVA software package (Bruker-AXS, 2007) and the ICDD-PDF 4 database. Quantitative Rietveld analyses based on least squares fitting of the weighted f-factors of all observed and calculated XRD peaks were performed using the TOPAZ software. This method yielded data about the exact particulates phase composition and components' crystallites size.

Scanning electron microscope (SEM) studies were carried out using a Hitachi S-5200 field emission SEM, generally operated at an accelerating voltage of 2.0 and 10.0 kV, coupled with a PGT EDS system and PGT Spirit software for elemental mapping and EDS.

Particles size distributions were measured using a Honeywell X100 series Microtrac Particle Size Analyzer and Automated Small Volume Recirculator (ASVR), capable of analyzing particle mixtures in the size range of 0.12 to 704 microns. The powders were prepared in a water suspension with Darvan C and sonicated externally using a Branson 450 Sonic Horn.

Photoluminescence spectra of the powders were recorded using a bench top spectrofluorometer (QuantaMaster™, Photon Technology International). The excitation and emission bandwidths were held constant yielding a measurement relative standard deviation of 5% for all samples. The spectrofluorometer is outfitted to measure phosphorescence lifetime as well. In this configuration the sample is irradiated with a flash lamp and the resulting intensity temporal profile is measured with a time gated photo detector. In either measurement, optical filters are used to remove undesirable stray light. Photoluminescence spectra were recorded using excitation with 365 and 254 nm UV, and the lifetimes with 365 nm UV, respectively.

Example 1

Single phase particulate materials having the compositions $(Y_{0.92}Eu_{0.08})_2O_3$ and $(Y_{0.92}Eu_{0.08})_3PO_7$ were produced by spray pyrolysis and were used to produce two different physical mixtures having the compositions (i) 35.5 wt % $(Y_{0.92}Eu_{0.08})_2O_3$+64.5 wt % $(Y_{0.92}Eu_{0.08})_3PO_7$ and (ii) 26 wt % $(Y_{0.92}Eu_{0.08})_2O_3$+74 wt % $(Y_{0.92}Eu_{0.08})_3PO_7$.

In addition, spray pyrolysis was employed to produce two two-phase composite particulate materials having the same compositions as the physical mixtures, namely $(Y_{0.92}Eu_{0.08})_2O_3$: $(Y_{0.92}Eu_{0.08})_3PO_7$=35.5:64.5 wt % and 26:74 wt %, respectively. The compositions of the physical mixtures and composite materials are summarized in Table 2.

TABLE 2

| Sample | ID code |
|---|---|
| Composite $(Y_{0.92}Eu_{0.08})_2O_3:(Y_{0.92}Eu_{0.08})_3PO_7 = 35.5:64.5$ wt % | C-1 |
| Composite $(Y_{0.92}Eu_{0.08})_2O_3:(Y_{0.92}Eu_{0.08})_3PO_7 = 26.5:73.5$ wt % | C-2 |
| Mixture $(Y_{0.92}Eu_{0.08})_2O_3:(Y_{0.92}Eu_{0.08})_3PO_7 = 35.5:64.5$ wt % | M-1 |
| Mixture $(Y_{0.92}Eu_{0.08})_2O_3:(Y_{0.92}Eu_{0.08})_3PO_7 = 26.5:73.5$ wt % | M-2 |

Figure 1:
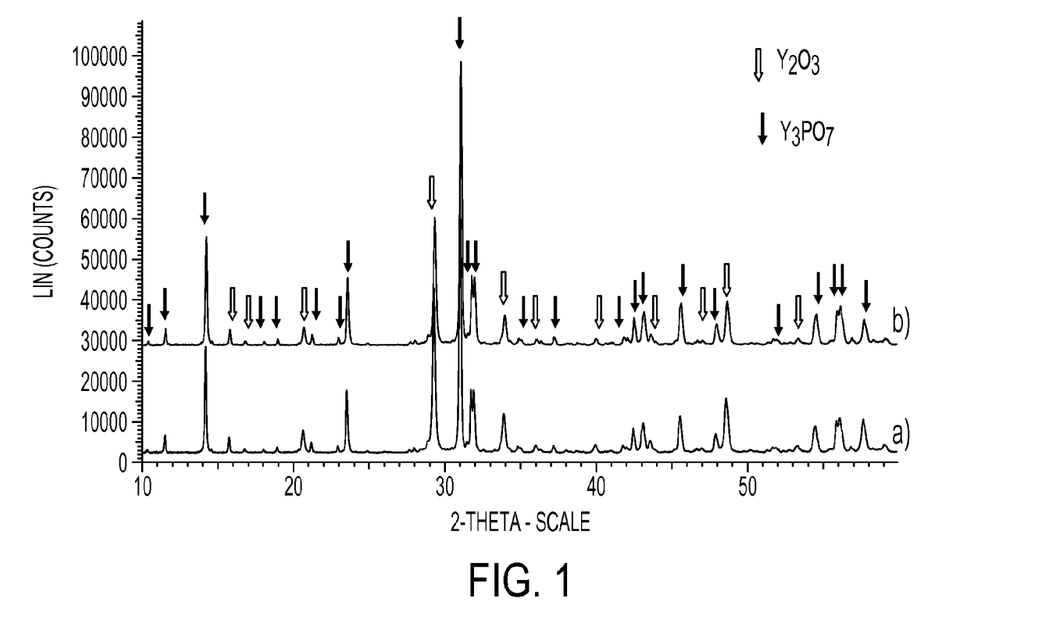

Powder X-ray diffraction (XRD) analysis of the composite materials confirmed the presence of two crystalline phases in both composite materials—$(Y_{0.92}Eu_{0.08})_2O_3$ and $(Y_{0.92}Eu_{0.08})_3PO_7$ (see FIG. 1). $(Y_{0.92}Eu_{0.08})_3PO_7$ was identified as a new phase isostructural to $Dy_3PO_7$ and consequent Rietveld structure refinement yielded the following parameters: S.G. Cm, a=12.6407 Å, b=12.6309 Å, c=11.9895 Å, β=108.75°, $R_{Bragg}$=4.3%, $R_{wp}$=6.7%.

Figure 2:
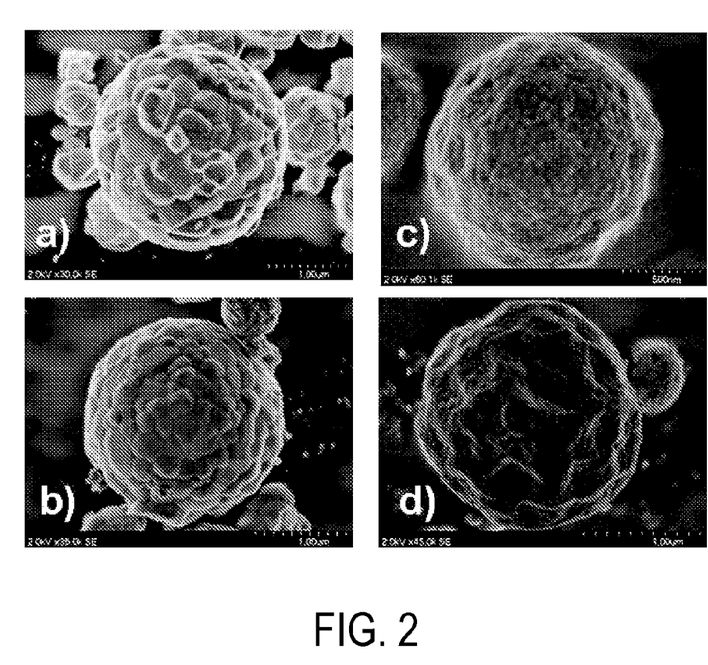
FIGS. 2(a) to (d) are SEM images of pure $(Y_{0.92}Eu_{0.08})$ (FIG. 2a), pure $(Y_{0.92}Eu_{0.08})_3PO_7$ (FIG. 2b), composite C-1 (FIG. 2c) and composite C-2 (FIG. 2d).

Quantitative Rietveld analysis of the XRD patterns confirmed the target compositions of the composites, for example $(Y_{0.92}Eu_{0.08})_2O_3$=35.6 wt % and $(Y_{0.92}Eu_{0.08})_3PO_7$=64.4 wt % for C-1 (theoretical values: 35.5 wt % and 64.5 wt %, respectively) [see FIG. 2]. The Eu distribution in the two phases was confirmed in the two components and the composite material by least squares fitting of the weighted f-factors of all observed and calculated XRD peaks—the lower the $R_W$ value the better the fit. For example the free variation of the Y:Eu ratio in $(Y_{0.92}Eu_{0.08})_2O_3$ yielded occupancy factors of Y=0.93 and Eu=0.08 which practically match the theoretical ones.

In a similar way, the best fit ($R_w$=7.34%) composite C-1 was achieved assuming statistical distribution of Eu in both components, followed by $R_w$=7.55% for the cases assuming Eu presence in only one of the components and the worst fit yielding $R_w$=7.55% resulted from the assumption that there is no Eu in any of the two components.

Scanning electron microscopy (SEM-EDX) analyses confirmed that both single phase components, $(Y_{0.92}Eu_{0.08})_2O_3$ and $(Y_{0.92}Eu_{0.08})_3PO_7$, were mixed within the composite particles forming individual micro crystallites less than 50 nm—much smaller than those of the pure components (200-400 nm) made by the same process (see FIG. 2).

Particles size distribution (PSD) studies confirmed that the composite materials have a narrow PSD within the range 1-5 microns and average particles diameter d-50 of about 2 microns, as shown in Table 3 below.

TABLE 3

PSD (micrometers) of the composites C-1 and C-2

| Percentiles | C-1 | C-2 |
|---|---|---|
| 10% | 1.06 | 0.96 |
| 50% | 1.87 | 1.58 |
| 95% | 4.62 | 3.81 |

Figure 3:
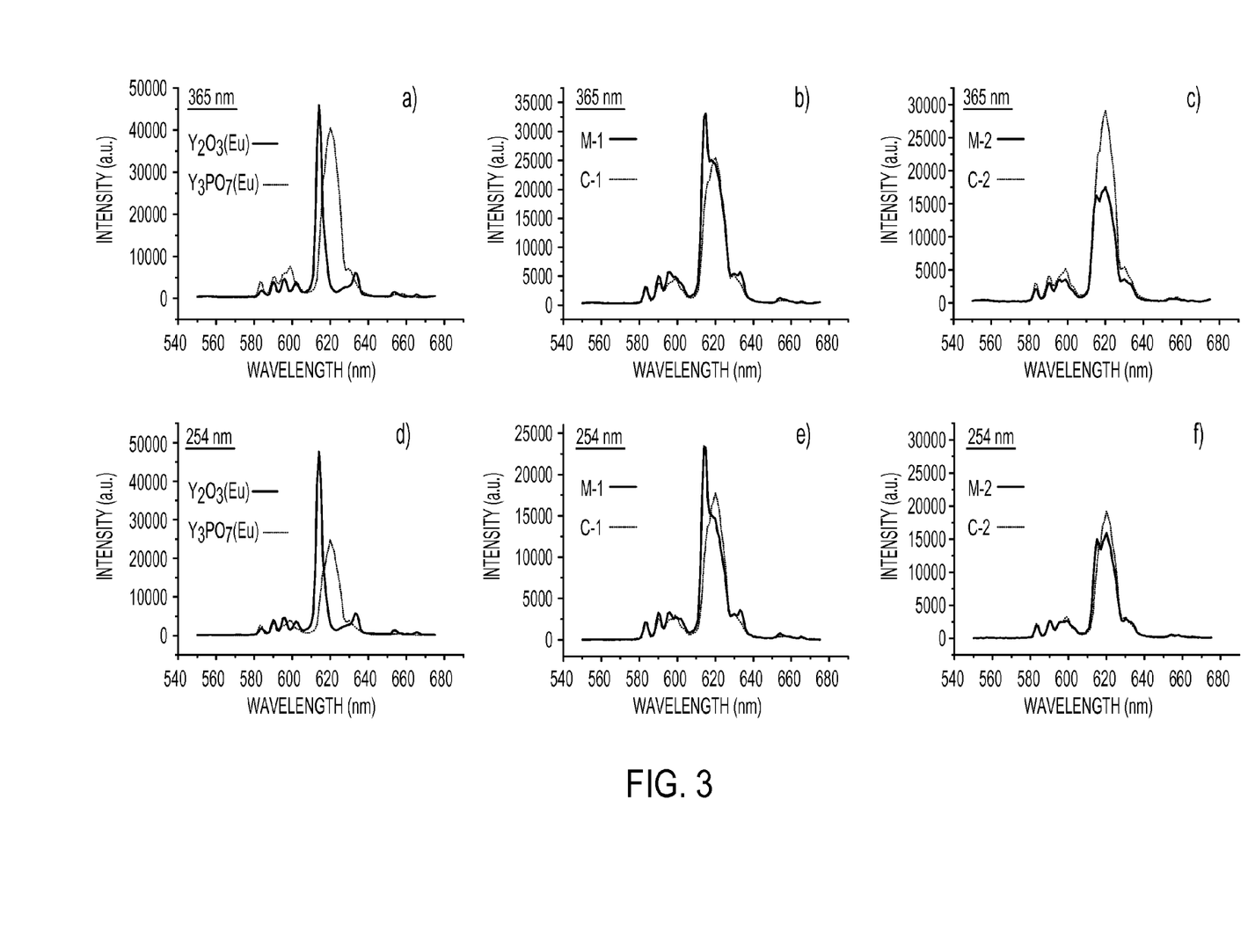

The photoluminescence (PL) emission spectra of the composites C-1 and C-2 after excitation with 365 and 254 nm UV light are compared to those of the mixtures with the same composition (M-1 and M-2) and the pure $(Y_{0.92}Eu_{0.08})_2O_3$ and $(Y_{0.92}Eu_{0.08})_3PO_7$ components in FIG. 3.

The steady state PL spectra of the individual components show strong peaks with maxima at 614 nm for $(Y_{0.92}Eu_{0.08})_2O_3$ and 620 nm for $(Y_{0.92}Eu_{0.08})_3PO_7$, respectively. The spectra of the composites C-1 and C-2 show broad peaks with maxima at 620 nm and shoulders at 614 nm. Overall, the spectra can be described as being closer to that of the $(Y_{0.92}Eu_{0.08})_3PO_7$ component with weaker effects arising from the $(Y_{0.92}Eu_{0.08})_2O_3$ component. This shows that the PL spectra of the composite materials are dominated by the emission of heavier mass fraction of $(Y_{0.92}Eu_{0.08})_3PO_7$ which is consistent with the compositions of C-1 and C-2, $(Y_{0.92}Eu_{0.08})_3PO_7$=64.4 and 73.5 wt %, respectively. In contrast, the PL spectra of the mixtures M-1 and M-2 show peaks with maxima at 614 nm and shoulders at 620 nm, i.e. these are dominated by the emission of $(Y_{0.92}Eu_{0.08})_2O_3$. This effect is more pronounced in the case of C-1 ($(Y_{0.92}Eu_{0.08})_2O_3$=35.6%) and decreases with the decrease of the mass fraction of $(Y_{0.92}Eu_{0.08})_2O_3$ (C-2: $(Y_{0.92}Eu_{0.08})_2O_3$=26.5%).

The integral intensity of all samples is a function of the crystallites size and hence depends on the relative area of the grain boundaries and the amounts of crystal lattice defects. The measurements of the dynamic property lifetime (τ) of the same species show more complex relations. It is proportional to the mass fraction and to the crystallites size of the individual components.

Example 2

Single phase materials have the compositions $(Y_{0.92}Eu_{0.08})_2O_3$, $(Y_{0.92}Eu_{0.08})_3PO_7$, $(Y_{0.92}Eu_{0.08})PO_4$ and three three-phase composite particulate materials containing $(Y_{0.92}Eu_{0.08})_2O_3$, $(Y_{0.92}Eu_{0.08})_3PO_7$ and $(Y_{0.92}Eu_{0.08})PO_4$ in different ratios were produced by spray pyrolysis. In addition, three physical mixtures with compositions identical to those of the composite materials were produced by mixing the pure $(Y_{0.92}Eu_{0.08})_2O_3$, $(Y_{0.92}Eu_{0.08})_3PO_7$ and $(Y_{0.92}Eu_{0.08})PO_4$ in the desired ratios. The compositions of the physical mixtures and composite materials are summarized in Table 4.

TABLE 4

| Sample | ID code |
|---|---|
| Composite $(Y_{0.92}Eu_{0.08})_2O_3:(Y_{0.92}Eu_{0.08})_3PO_7:(Y_{0.92}Eu_{0.08})_3PO_4 = 34:37:29$ wt % | C-3 |
| Composite $(Y_{0.92}Eu_{0.08})_2O_3:(Y_{0.92}Eu_{0.08})_3PO_7:(Y_{0.92}Eu_{0.08})_3PO_4 = 40:49:11$ wt % | C-4 |
| Composite $(Y_{0.92}Eu_{0.08})_2O_3:(Y_{0.92}Eu_{0.08})_3PO_7:(Y_{0.92}Eu_{0.08})_3PO_4 = 16:78:5$ wt % | C-5 |
| Mixture $(Y_{0.92}Eu_{0.08})_2O_3:(Y_{0.92}Eu_{0.08})_3PO_7:(Y_{0.92}Eu_{0.08})_3PO_4 = 34:37:29$ wt % | M-3 |
| Mixture $(Y_{0.92}Eu_{0.08})_2O_3:(Y_{0.92}Eu_{0.08})_3PO_7:(Y_{0.92}Eu_{0.08})_3PO_4 = 40:49:11$ wt % | M-4 |
| Mixture $(Y_{0.92}Eu_{0.08})_2O_3:(Y_{0.92}Eu_{0.08})_3PO_7:(Y_{0.92}Eu_{0.08})_3PO_4 = 16:78:5$ wt % | M-5 |

Figure 4:
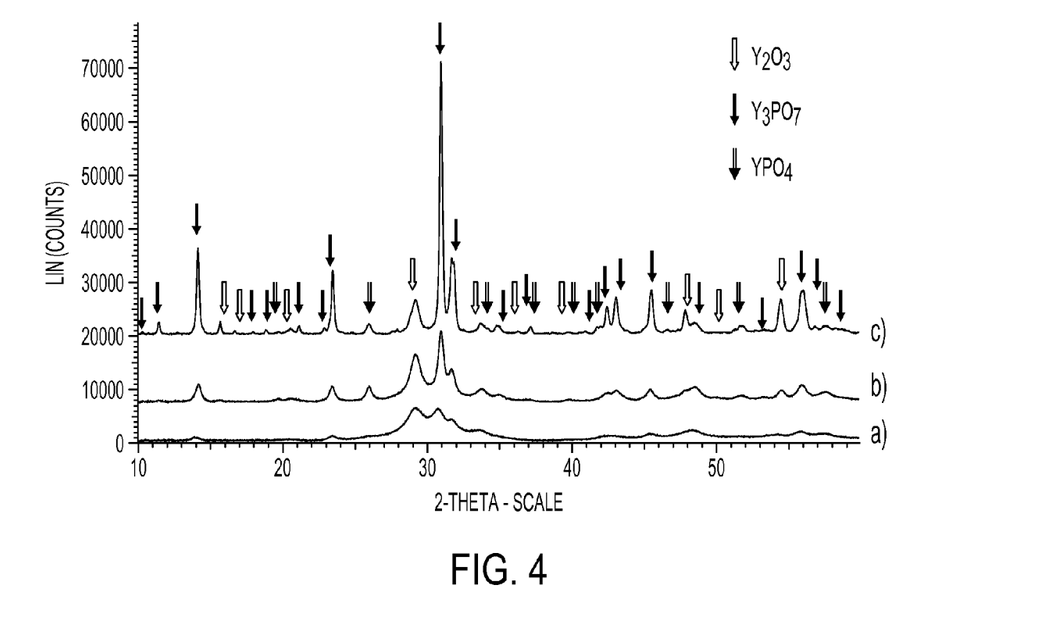
FIGS. 4(a) to (c) are XRD patterns of the composites C-3, C-4 and C-5 respectively of Example 2.

XRD analysis of the composite materials confirmed the presence of three crystalline phases—$(Y_{0.92}Eu_{0.08})_2O_3$, $(Y_{0.92}Eu_{0.08})_3PO_7$ and $(Y_{0.92}Eu_{0.08})PO_4$, see FIG. 4. The exact ratios of the crystalline components cited in Table 4 were determined by Rietveld analysis of the corresponding XRD patterns.

Figure 5:
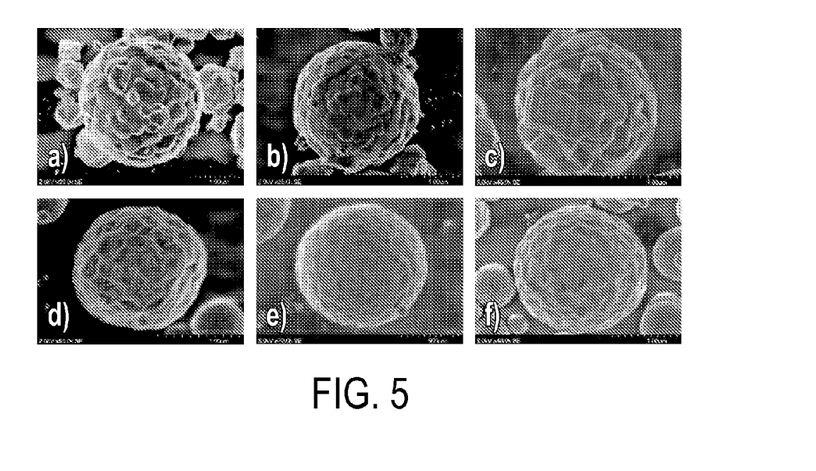
FIGS. 5(a) to (f) are SEM images of pure $(Y_{0.92}Eu_{0.08})_2O_3$ (FIG. 5a), pure $(Y_{0.92}Eu_{0.08})_3PO_7$ (FIG. 5b), pure $(Y_{0.92}Eu_{0.08})PO_4$ (FIG. 5c), composite C-3 (FIG. 5d), composite C-4 (FIG. 5e) and composite C-5 (FIG. 5l).

Scanning electron microscopy (SEM-EDX) analyses confirmed that the single phase components—$(Y_{0.92}Eu_{0.08})_2O_3$, $(Y_{0.92}Eu_{0.08})_3PO_7$ and $(Y_{0.92}Eu_{0.08})PO_4$ formed individual micro crystallites within the composite particles of less than 50 nm—much smaller than those of the pure components made by the same process, see FIG. 5.

Particles size distribution (PSD) studies confirmed that the three composite materials have a narrow PSD within the range 1-3 microns and average particles diameter d-50 of about 1.3 microns, as shown in Table 5.

TABLE 5

PSD (micrometers) of the composites C-3, C-4 and C-5

| Percentiles | C-3 | C-4 | C-5 |
|---|---|---|---|
| 10% | 0.86 | 0.89 | 0.92 |
| 50% | 1.30 | 1.31 | 1.35 |
| 95% | 2.96 | 2.84 | 2.99 |

Figure 6:
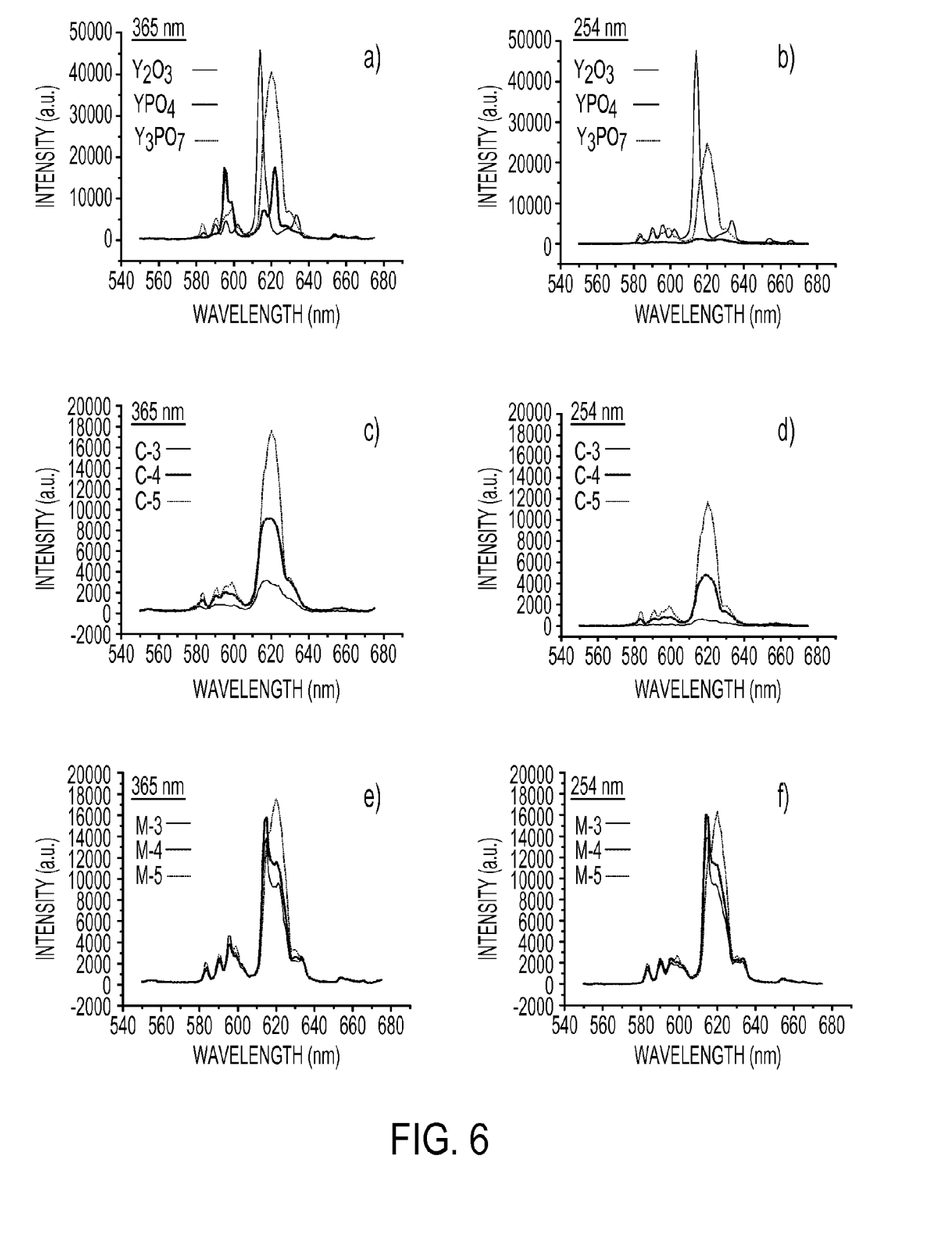
FIGS. 6(a) to (c) compare the PL emission spectra of the individual pure $(Y_{0.92}Eu_{0.08})_2O_3$, $(Y_{0.92}Eu_{0.08})PO_4$ and $(Y_{0.92}Eu_{0.08})_3PO_7$ components (FIG. 6a), the composites C-3, C-4 and C-5 (FIG. 6b), and the mixtures with identical compositions M-3, M-4 and M-5 (FIG. 6c) after excitation with 365 nm UV light.
FIGS. 6(d) to (f) compare the PL emission spectra of the individual pure $(Y_{0.92}Eu_{0.08})_2O_3$, $(Y_{0.92}Eu_{0.08})PO_4$ and $(Y_{0.92}Eu_{0.08})_3PO_7$ components (FIG. 6d), the composites C-3, C-4 and C-5 (FIG. 6e), and the mixtures with identical compositions M-3, M-4 and M-5 (FIG. 6f) after excitation with 254 nm UV light.

The photoluminescence (PL) emission spectra after excitation with 365 and 254 nm UV light of the pure $(Y_{0.92}Eu_{0.08})_2O_3$, $(Y_{0.92}Eu_{0.08})PO_4$ and $(Y_{0.92}Eu_{0.08})_3PO_7$ components are compared to those of the composites C-3, C-4 and C-5 and the mixtures with identical compositions M-3, M-4 and M-5 in FIG. 6.

The steady state PL spectra of the individual components show strong peaks with maxima at 614 nm for $(Y_{0.92}Eu_{0.08})_2O_3$, 595 and 625 nm for $(Y_{0.92}Eu_{0.08})_3PO_7$ and 620 nm for $(Y_{0.92}Eu_{0.08})_3PO_7$, respectively. It is worthy of note that while the relative PL emission intensities of the pure components after excitation at 365 nm are comparable, the intensity of pure $(Y_{0.92}Eu_{0.08})PO_4$ after excitation at 254 nm is close to zero, see FIGS. 6(a) and (b).

The spectra of the composites C-3, C-4 and C-5 show broad peaks with maxima centered at 620 nm and can be described as being closer to that of the $(Y_{0.92}Eu_{0.08})_3PO_7$ component with weaker effects arising from the other two components. This shows that the composites' PL spectra are dominated by the emission of the component with the heavier mass fraction which is consistent with the corresponding compositions in Table 5. In contrast, the PL spectra of the mixtures M-3 and M-4 show peaks with maxima at 614 nm and shoulders at 620 nm, i.e. these are dominated by the emission of $(Y_{0.92}Eu_{0.08})_2O_3$ which mass fraction is comparable to that of $(Y_{0.92}Eu_{0.08})_3PO_7$. In the case of M-5 the spectrum is again dominated by the heaviest fraction $(Y_{0.92}Eu_{0.08})_3PO_7$.

The integral intensity of all samples is a function of the crystallites size and, hence, depends on the relative area of the grain boundaries and the amounts of crystal lattice defects. The measurement of the dynamic property lifetime (τ) of the same species shows more complex relations. It is proportional to the mass fraction and to the crystallites size of the individual components.

Example 3

Single phase particulate material of composition $(Y_{0.92}Eu_{0.08})_2O_3$ and $(Y_{0.92}Eu_{0.08})_4Al_2O_9$ and a two-phase composite particulate material of composition 22.8 wt % $(Y_{0.92}Eu_{0.08})_2O_3/77.2$ wt % $(Y_{0.92}Eu_{0.08})_4Al_2O_9$ were produced by spray pyrolysis. In addition, a physical mixture with composition identical to that of the composite material have been made by mixing pure $(Y_{0.92}Eu_{0.08})_2O_3$ and $(Y_{0.92}Eu_{0.08})_4Al_2O_9$ in the same ratio, as shown in Table 6.

TABLE 6

| Sample | ID code |
|---|---|
| Composite $(Y_{0.92}Eu_{0.08})_2O_3$:$(Y_{0.92}Eu_{0.08})_4Al_2O_9$ = 22.8:77.2 wt % | C-6 |
| Mixture $(Y_{0.92}Eu_{0.08})_2O_3$:$(Y_{0.92}Eu_{0.08})_4Al_2O_9$ = 22.8:77.2 wt % | M-6 |

Figure 7:
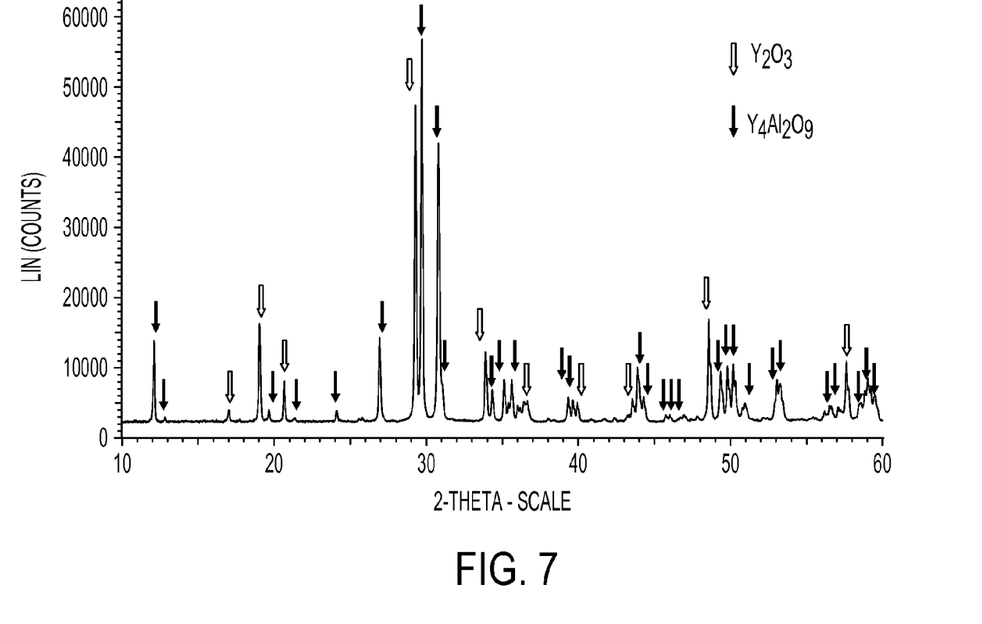
FIG. 7 is an XRD pattern of composite C-6 of Example 3.

Powder XRD analysis of the composite material C-6 confirmed the presence of two crystalline phases in the composite material—$(Y_{0.92}Eu_{0.08})_2O_3$ and $(Y_{0.92}Eu_{0.08})_4Al_2O_9$, see FIG. 7. Quantitative Rietveld analysis of the XRD pattern yielded the exact ratio of the components, $(Y_{0.92}Eu_{0.08})_2O_3$:$(Y_{0.92}Eu_{0.08})_4Al_2O_9$=22.8:77.2 wt %.

Figure 8:
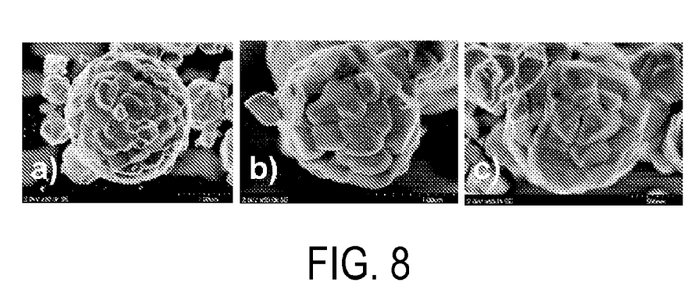

Scanning electron microscopy (SEM-EDX) analyses confirmed that both single phase components, $(Y_{0.92}Eu_{0.08})_2O_3$ and $(Y_{0.92}Eu_{0.08})_4Al_2O_9$, were mixed within the composite particles forming individual micro crystallites comparable to those of the pure components (100-300 nm) made by the same process, see FIG. 8.

Particles size distribution (PSD) studies confirmed that the composite materials have a narrow PSD within the range 0.7-3.7 microns and average particles diameter d-50 of about 1.4 microns, as shown in Table 7.

TABLE 7

PSD of composite C-6

| Percentiles | Microns |
|---|---|
| 10% | 0.69 |
| 50% | 1.35 |
| 95% | 3.72 |

Figure 9:
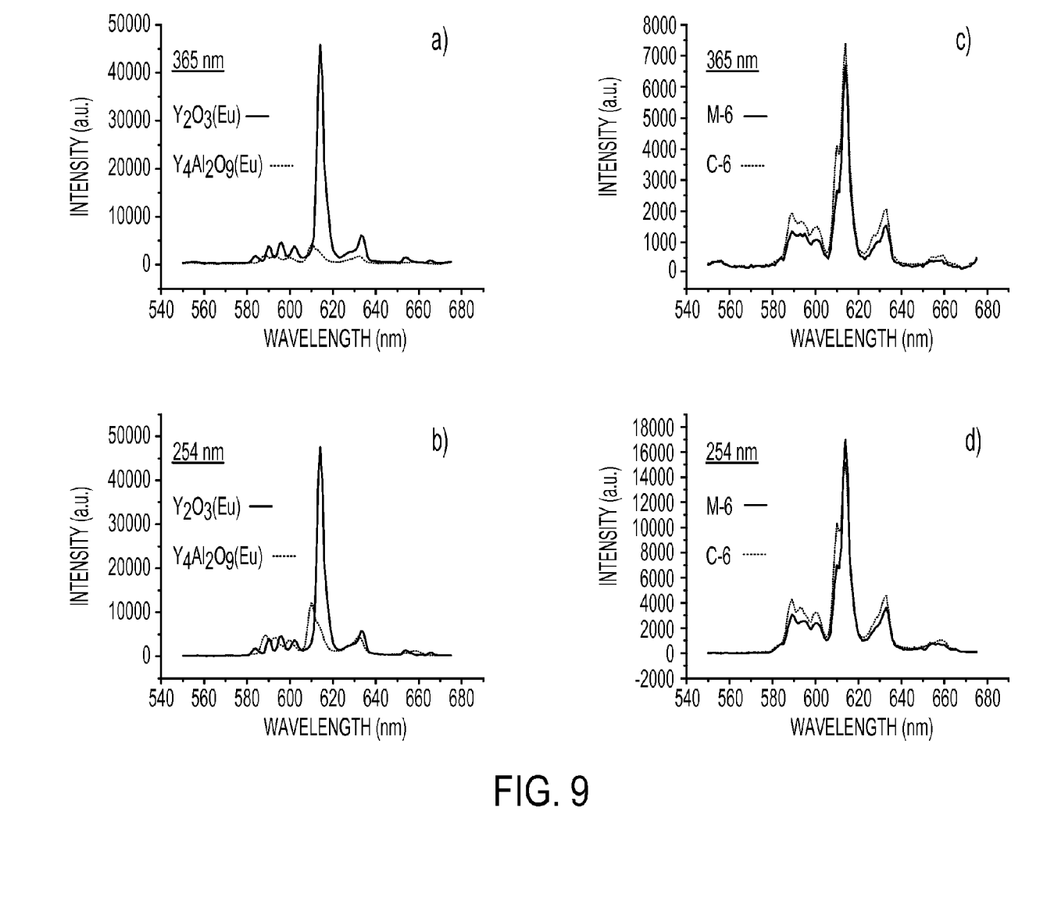

The photoluminescence (PL) emission spectra of composite C-6 after excitation with 365 and 254 nm UV light are compared to those of pure $(Y_{0.92}Eu_{0.08})_2O_3$ and $(Y_{0.92}Eu_{0.08})_4Al_2O_9$ samples in FIG. 9.

The steady state PL spectra of the individual components show strong peaks with maxima at 614 nm for $(Y_{0.92}Eu_{0.08})_2O_3$ and 610 nm for $(Y_{0.92}Eu_{0.08})_4Al_2O_9$, respectively. The spectra of the composite C-6 and the mixture M-6 show very similar peaks with maxima at 614 nm and shoulders at 610 nm. Overall, the spectra can be described as a linear combination of those of the individual components. It is worth noticing that the satellite peaks at 590-600 and 630 nm have higher intensity when excited with 254 nm than 365 nm UV light, which is consistent with the stronger emission of $(Y_{0.92}Eu_{0.08})_4Al_2O_9$ when excited with 254 nm UV light.

The integral intensities of the composite C-6 and the corresponding mixture M-6 are a function of the crystallites size and, hence, depend on the relative area of the grain boundaries and the amounts of crystal lattice defects. The measurements of the dynamic property lifetime (τ) of the same species show more complex relations. It is proportional to the mass fraction and to the crystallites size of the individual components.

Example 4

Single phase particulate materials of composition $(Y_{0.92}Eu_{0.08})_3Al_5O_{12}$ and $(Y_{0.92}Eu_{0.08})_4Al_2O_9$ and two two-phase composite particulate materials of compositions $Y_{0.92}Eu_{0.08})_3Al_5O_{12}/(Y_{0.92}Eu_{0.08})_4Al_2O_9$ in different ratios as shown in Table 6 were produced by spray pyrolysis. In addition, two physical mixtures with compositions identical to those of the composite materials were produced by mixing pure $(Y_{0.92}Eu_{0.08})_3Al_5O_{12}$ and $(Y_{0.92}Eu_{0.08})_4Al_2O_9$ in the desired ratios, again as shown in Table 8.

TABLE 8

| Sample | ID code |
|---|---|
| Composite $(Y_{0.92}Eu_{0.08})_3Al_5O_{12}$:$(Y_{0.92}Eu_{0.08})_4Al_2O_9$ = 91.4:8.6 wt % | C-7 |
| Composite $(Y_{0.92}Eu_{0.08})_3Al_5O_{12}$:$(Y_{0.92}Eu_{0.08})_4Al_2O_9$ = 21.8:78.2 wt % | C-8 |

TABLE 8-continued

| Sample | ID code |
|---|---|
| Mixture $(Y_{0.92}Eu_{0.08})_3Al_5O_{12}$:$(Y_{0.92}Eu_{0.08})_4Al_2O_9$ = 91.4:8.6 wt % | M-7 |
| Mixture $(Y_{0.92}Eu_{0.08})_3Al_5O_{12}$:$(Y_{0.92}Eu_{0.08})_4Al_2O_9$ = 21.8:78.2 wt % | M-8 |

Figure 10:
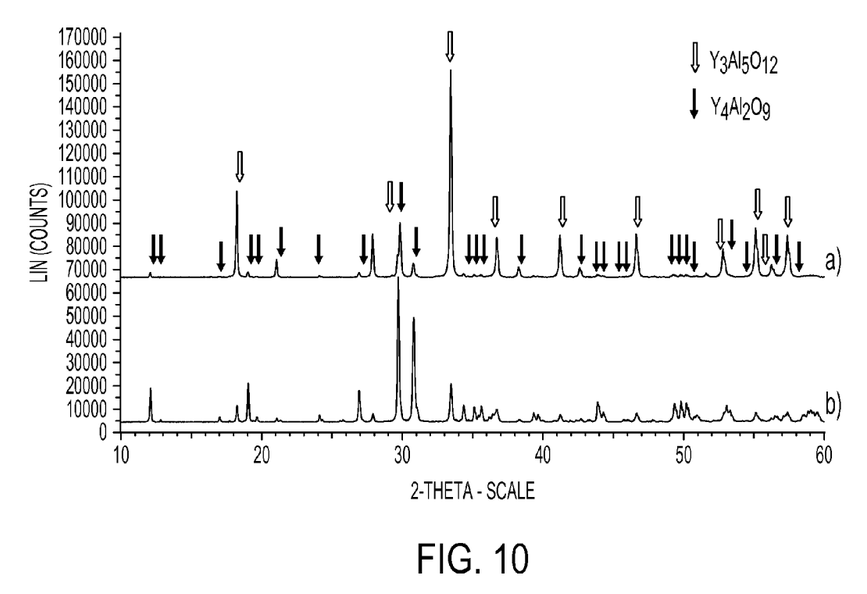

Powder XRD analysis of the composite materials confirmed the presence of two crystalline phases in both composite materials—$(Y_{0.92}Eu_{0.08})_3Al_5O_{12}$ and $(Y_{0.92}Eu_{0.04})_4Al_2O_9$, see FIG. 10. Quantitative Rietveld analysis of the XRD patterns yielded the exact compositions of the composites as given in Table 8.

Figure 11:
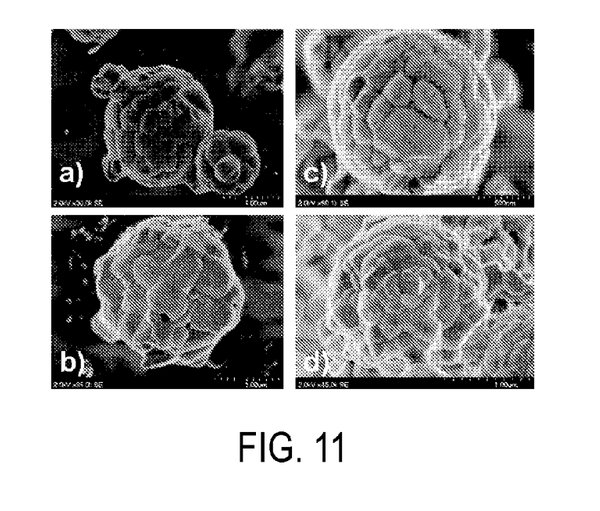
FIGS. 11(a) to (d) are SEM images of pure $(Y_{0.92}Eu_{0.08})_3Al_5O_{12}$, pure $(Y_{0.92}Eu_{0.08})_4Al_2O_9$, composite C-7 and composite C-8 respectively.

Scanning electron microscopy (SEM-EDX) analyses confirmed that both single phase components, $(Y_{0.92}Eu_{0.08})_3Al_5O_{12}$ and $(Y_{0.92}Eu_{0.08})_4Al_2O_9$, were mixed within the composite particles forming individual micro crystallites that are comparable to those of the pure components (100-300 nm) made by the same process, see FIG. 11.

Particles size distribution (PSD) studies confirmed that the composite materials have a narrow PSD within the range 1-5 microns and average particles diameter d-50 of about 2 microns, see Table 9.

TABLE 9

PSD (micrometers) of the composites C-7 and C-8

| Percentiles | C-7 | C-8 |
|---|---|---|
| 10% | 0.96 | 0.75 |
| 50% | 1.86 | 1.42 |
| 95% | 4.61 | 5.13 |

Figure 12:
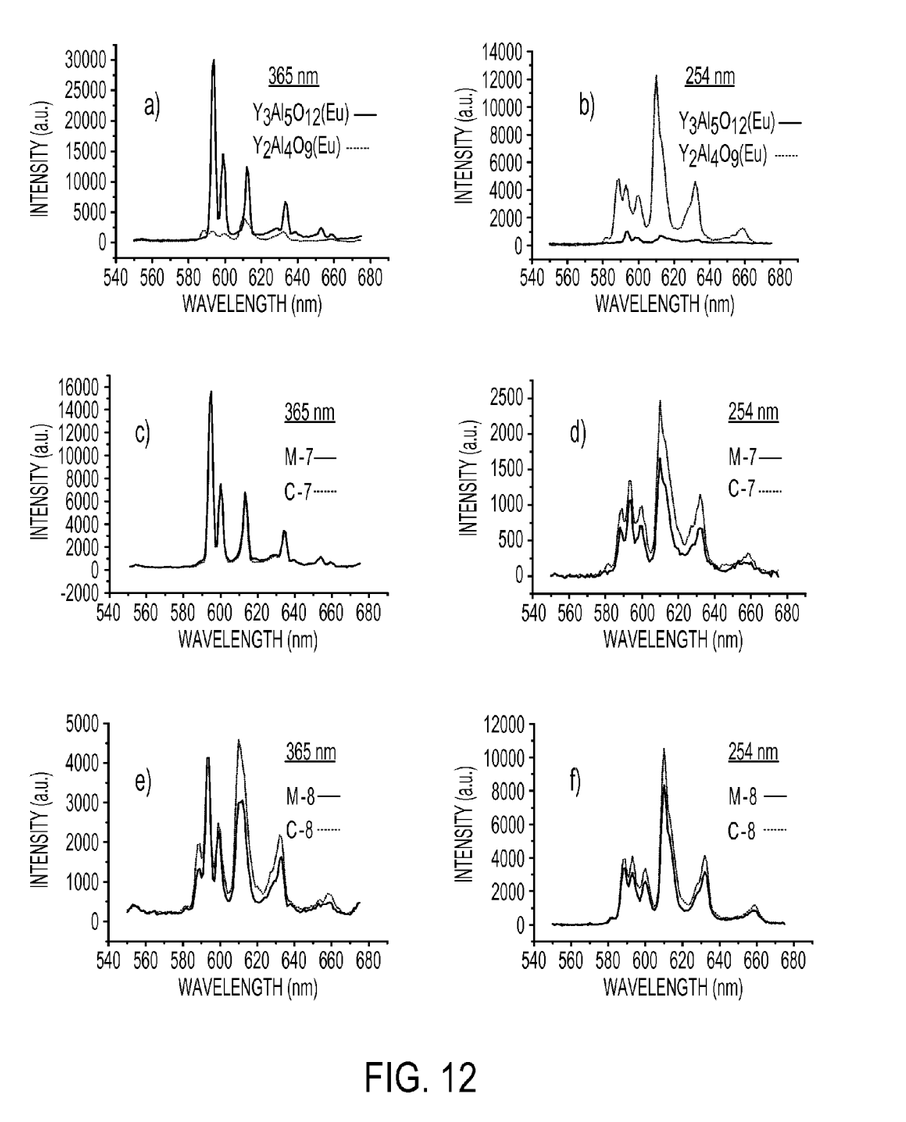
FIGS. 12(a) to (c) compare the PL emission spectra of the individual pure $(Y_{0.92}Eu_{0.08})_2Al_5O_{12}$ and $(Y_{0.92}Eu_{0.08})_4Al_2O_9$ components (FIG. 12a), the mixture M7 and the composite C-7 (FIG. 12b), and the mixture M8 and the composite C8 (FIG. 12c) after excitation with 365 nm UV light.
FIGS. 12(d) to (f) compare the PL emission spectra of the individual pure $(Y_{0.92}Eu_{0.08})_3Al_5O_{12}$ and $(Y_{0.92}Eu_{0.08})_4Al_2O_9$ components (FIG. 12d), the mixture M7 and the composite C-7 (FIG. 12e), and the mixture M8 and the composite C8 (FIG. 12f) after excitation with 254 nm UV light.

The photoluminescence (PL) emission spectra of the composites C-7 and C-8 after excitation with 365 and 254 nm UV light are compared to those of pure $(Y_{0.92}Eu_{0.08})_3Al_5O_{12}$ and $(Y_{0.92}Eu_{0.08})_4Al_2O_9$ samples in FIG. 12.

The steady state PL spectra of the individual components when excited with 365 nm UV show strong peaks with maxima at 595, 600, 615 and 635 nm for $(Y_{0.92}Eu_{0.08})_3Al_5O_{12}$ and only a weak peak at 610 nm for $(Y_{0.92}Eu_{0.08})_4Al_2O_9$, respectively. In contrast, when excited with 254 nm UV, the intensity of the emission spectra of $(Y_{0.92}Eu_{0.08})_3Al_5O_{12}$ is virtually zero while that of $(Y_{0.92}Eu_{0.04}Al_2O_9$ shows strong peaks with maxima at 585-605, 615, 630 and 660 nm. The spectra of the composites C-7 and C-8 and the mixtures M-7 and M-8 show strong peaks with maxima that coincide with the maxima for $(Y_{0.92}Eu_{0.08})_3Al_5O_{12}$ and $(Y_{0.92}Eu_{0.08})_4Al_2O_9$ when excited with 365 and 254 nm, respectively. This shows that PL spectra of the composites are dominated by the emission of the component with the heavier mass fraction which is consistent with the corresponding compositions given in Table 8.

The integral intensities of all samples are a function of the crystallites size and, hence, depend on the relative area of the grain boundaries and the amounts of individual crystal lattices defects. The measurements of the dynamic property lifetime ($\tau$) of the same species show more complex relations. It is proportional to the mass fraction and to the crystallites size of the individual components.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A method for authenticating and differentiating between a series of articles, the method comprising:
    applying to each article a security feature comprising a particulate composition comprising at least one particle having at least two different crystalline and/or glass phases, each phase comprising a host lattice and a dopant sensitive to electromagnetic radiation and the different phases simultaneously producing different responses on exposure to photons of the same energy, whereby the output from the particulate composition when exposed to said photons is the sum of the responses from the different phases;
    varying the ratio of the amounts of the different phases in the particulate compositions applied to the different articles whereby each article produces a different output on exposure to said photons of a given energy;
    exposing each article to on exposure to photons of said given energy;
    measuring the output from each article; and
    authenticating the articles.

2. The method of claim 1, wherein each phase is sensitive to electromagnetic radiation in the UV, visible or IR regions of the electromagnetic spectrum.

3. The method of claim 1, wherein the different phases produce different emission spectra on exposure to photons of the same energy.

4. The method of claim 3, wherein the different phases produce emission spectra with peaks at different wavelengths on exposure to said photons of the same energy.

5. The method of claim 3, wherein each phase produces an emission spectrum with multiple peaks on exposure to photons of the same energy and the ratio of the relative intensities of the peaks differs between the phases.

6. The method of claim 3, wherein the different phases emit radiation having different decay rates on exposure to said photons of the same energy.

7. The method of claim 1, wherein each phase of said at least one particle has a different selective absorbance to photons at the same wavelength.

8. The method of claim 1, wherein each phase of said at least one particle has a different extinction coefficient to photons at different wavelengths.

9. The method of claim 1, wherein the composition has an average particle size of less than about 10 µm.

10. The method of claim 9, wherein at least about 90 weight percent of the particles are not larger than twice said average particle size.

11. The method of claim 1, wherein the composition has an average particle size of from about 0.1 µm to about 3 µm.

12. The method of claim 1, wherein the composition is composed of substantially spherical particles.

13. The method of claim 1, wherein the article is selected from the group consisting of a credit card, a driver's license, a passport, a check, currency, a bond, a ticket, a tax stamps, a banknote, a cigarette pack tear tape, a security thread, and an identification card.

* * * * *